United States Patent [19]

Ambegaonkar et al.

[11] Patent Number: 4,891,223
[45] Date of Patent: Jan. 2, 1990

[54] CONTROLLED RELEASE DELIVERY COATING FORMULATION FOR BIOACTIVE SUBSTANCES

[75] Inventors: Anil S. Ambegaonkar, Hatfield; Roger A. Howells, Orefield, both of Pa.

[73] Assignee: Air Products and Chemicals, Inc., Allentown, Pa.

[21] Appl. No.: 92,743

[22] Filed: Sep. 3, 1987

[51] Int. Cl.$^4$ ............................................. A01N 25/34
[52] U.S. Cl. .................................... 424/408; 424/471; 424/473
[58] Field of Search ......................... 424/471, 473, 408

[56] References Cited

U.S. PATENT DOCUMENTS

| | | | |
|---|---|---|---|
| 3,845,770 | 11/1974 | Theeuwes et al. | 128/260 |
| 4,111,201 | 9/1978 | Theeuwes | 424/473 |
| 4,138,475 | 2/1979 | McAinsh et al. | 424/19 |
| 4,177,056 | 12/1979 | Mueller et al. | 71/93 |
| 4,235,236 | 11/1980 | Theeuwes | 424/473 |
| 4,327,725 | 5/1982 | Cortese et al. | 128/260 |
| 4,423,099 | 12/1983 | Mueller et al. | 428/35 |
| 4,681,755 | 7/1987 | Colombo et al. | 424/486 |

OTHER PUBLICATIONS

W. E. Roorda, "Zero-Order Release of Oxprenolol-HCl ... ", 13th Int'l Symposium, c. 1986.
Chemical Abstracts 108 (22): 192793o.
R. Baker, "Analysis of Oral Dosage Form Patents", 1939–1985, Membrane Technology and Research, c. 1987, Sections B and C.
Lonsdale and Baker, "Controlled Delivery—An Emerging Use For Membranes", *Chemtech*, Nov. 1975.
D. R. Paul, "Polymers in Controlled Release Technology", Chapter 1, ACS Symposium Series, *Polymers*, 1976.
M. Donbrow, "Design of Microcapsules—Release Kinetics and Mechanism", 13th Int'l Symposium on Controlled Release, 1986.
N. Graham et al., "Principles of Design of Hydrogel-Containing Programmed Delivery Devices", 13th Int'l Symposium, 1986.

*Primary Examiner*—William R. Dixon, Jr.
*Assistant Examiner*—Andrew Griffin
*Attorney, Agent, or Firm*—Willard Jones, II; James C. Simmons; William F. Marsh

[57] ABSTRACT

The present invention relates to a bioactive composition having a controlled, sustained release delivery pattern when contacted with a suitable surrounding media. The composition comprises a pharmaceutically, insecticidally, herbicidally or fertilizing bioactive material core, soluble in a given surrounding media, the core present in an amount at least sufficient for a total dosage during a specified treatment period; a first coating enveloping the bioactive material core comprising a polymer or a blend of polymers, said polymer or blend of polymers being swellable upon penetration by the surrounding media; and a second coating enveloping the first coating, the second coating comprising a polymer or a blend of polymers being water-insoluble and forming a semipermeable barrier to the inward diffusion of the surrounding media and the outward diffusion of the bioactive material dissolved in the surrounding media.

6 Claims, 11 Drawing Sheets

RUN NUMBER 4

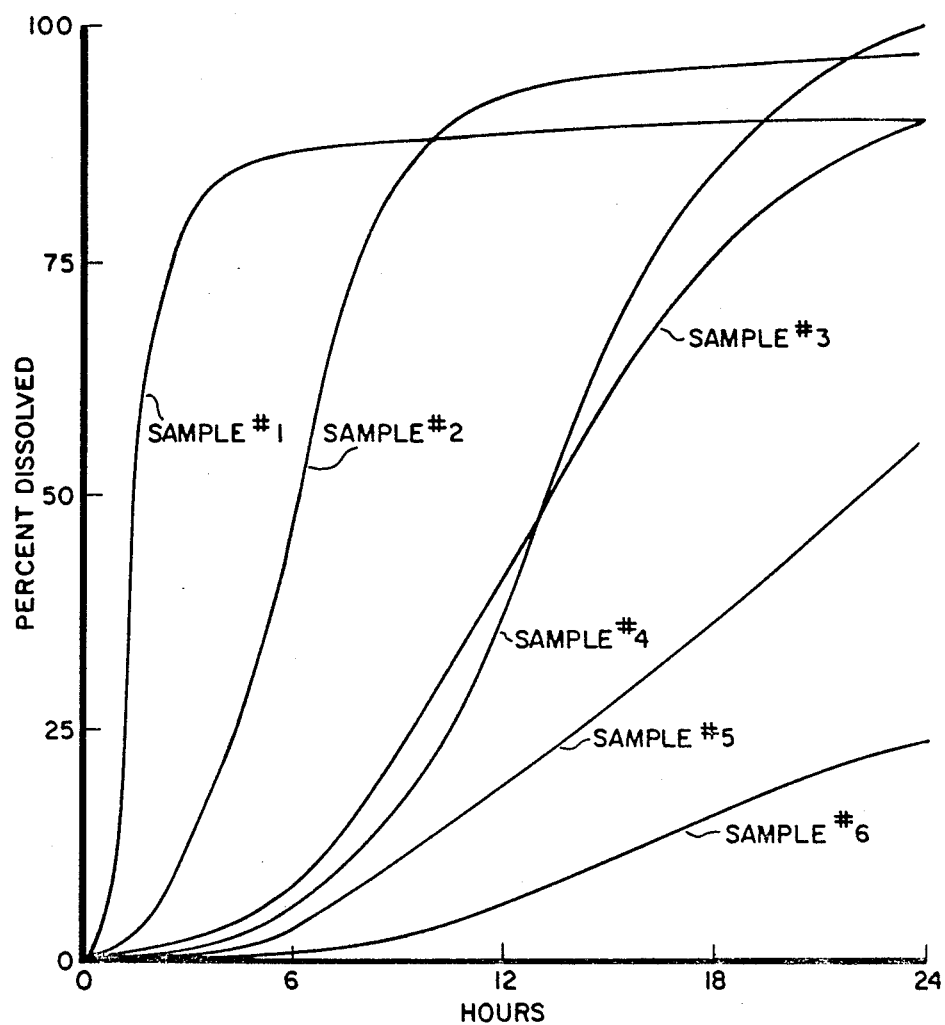

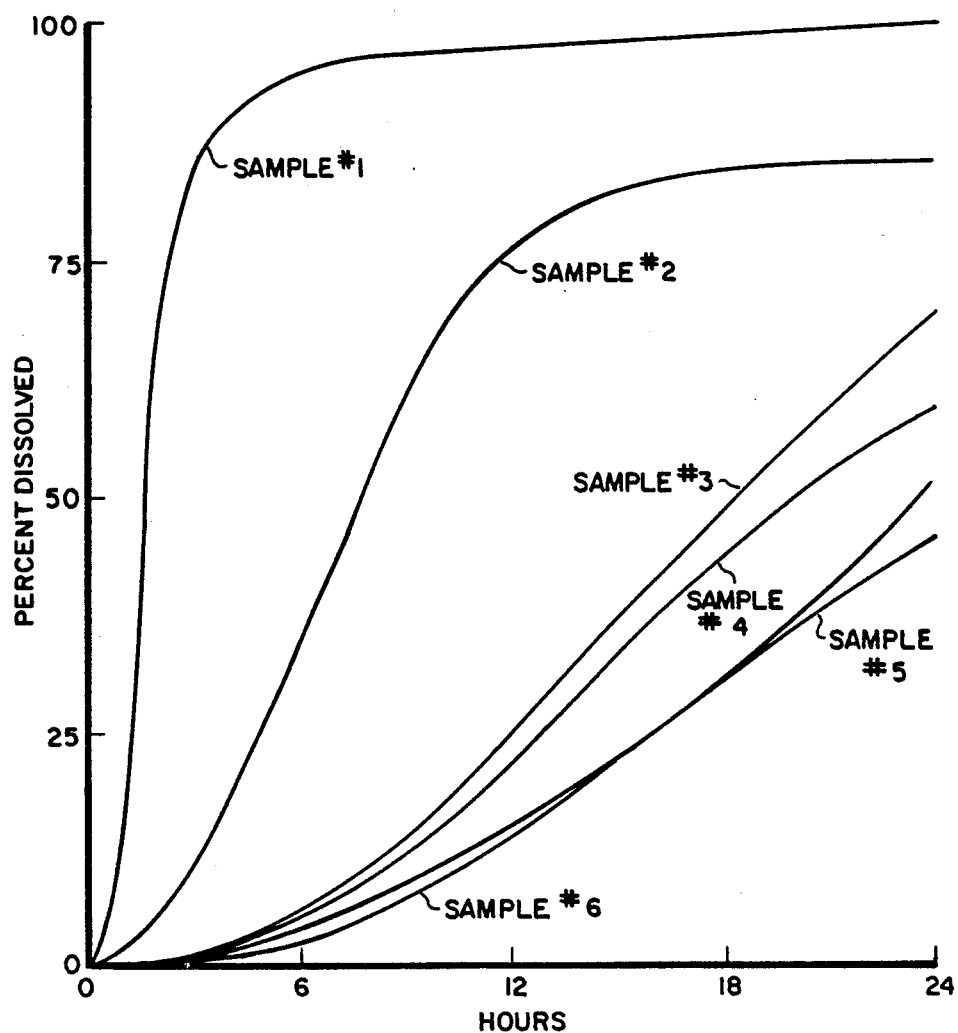

CONTROLLED RELEASE DELIVERY COATING FORMULATION FOR BIOACTIVE SUBSTANCES

TECHNICAL FIELD

The present invention relates to a coating formulation for the encapsulation of bioactive substances. More particularly, the present invention relates to a coating formulation for a bioactive substance which results in a first-order, fractional-order, zero-order, or biphasic release of the bioactive substance.

DEFINITIONS OF TECHNICAL TERMS

There are several technical terms which will be used repeatedly in this specification, in order to better understand the usage of these terms the following definitions are offered:

Immediate Release—A drug dosage form which releases its contents almost immediately after the drug comes in contact with alimentary fluids. Since most drugs are rapidly absorbed in the gastrointestinal (GI) tract (stomach) the immediate release type of dosage form causes a sharp rise in drug concentration in the body. Thereafter, depending upon the dosage frequency and the elimination kinetics of the drug, the drug concentration in the blood plasma decreases rapidly. This leads to peaks and valleys in the drug concentration profile in the body. The peaks are associated with toxic side effects, if any, whereas the valleys are associated with low therapeutic benefit to the drug user or recipient.

Sustained Release—A drug dosage form which releases its drug content gradually after the drug makes contact with alimentary fluids. This dampens the peaks and valleys that are observed with the Immediate Release version. The drug concentration is maintained in the body for longer periods of time, leading to reduction in the frequency of dosage, e.g., time-release theophylline. Most sustained release versions which are available in the market do not have a release mechanism which can produce uniform blood concentration levels for a prolonged period of time. Initially, the rate of drug release increases rapidly and is followed by a continuously declining rate of release at an exponential rate. This type of drug release is categorized as the first-order release mechanism.

Zero-Order Release—A drug delivery system which causes the drug to be released at a uniform rate independent of the drug concentration (in the dosage form) during the period of release. Such an ideal drug delivery system can produce uniform drug concentration levels for a prolonged period of time. The zero-order delivery system is capable of providing maximum therapeutic value while minimizing the side effects. It can also reduce the dosing frequency to once in twelve hours or once in twenty-four hours, thus improving the dosage compliance on the part of subjects.

Penetrant—Surrounding media such as water which diffuses into the drug delivery system to initiate the drug pharmacological effect.

Bioactive Substance—A pharmaceutical, pesticide or any other active ingredient to be encapsulated.

Semi-permeable Barrier—Primarily, a membrane which permits the diffusion of the external fluid into the bead core as well as the diffusion of the external fluid dissolved bioactive material into the surrounding media.

BACKGROUND OF THE INVENTION

In order to improve the therapeutic safety and efficacy of the immediate release drugs, the sustained-release dosage forms have been developed by the industry. These dosage forms are capable of dampening the peaks and valleys experienced with the immediate release dosage form of drugs. However, the sustained-release dosage forms do not give the ideal zero-order release of drugs in the body. Upon swallowing the sustained-release form of drugs, the drug concentration reaches a maximum value (maximum at time, $t_{max}$) and thereafter declines continuously at an exponential rate. Thus the sustained-release dosage forms do not produce a constant level of drug in the body, which is the desirable objective of most drug delivery systems. The ideal zero-order delivery system will release drug at a uniform rate and thus lead to constant drug levels in the body. This will maximize the therapeutic benefit to the subject while minimizing the toxic side effects associated with super therapeutic levels.

Several methods for producing a sustained-release delivery system are known in the art among these are the following.

Film-Coated Beads: Sustained-release drugs are made by encapsulating tiny beads of the drug substance in a semi-permeable membrane. Upon contact with the body fluids, the body fluids diffuse into the drug bead through the semi-permeable membrane and dissolve the drug substance. The solution of the drug dissolved in body fluids (water) then diffuses out through the membrane. The rate of drug diffusion is dependent upon the drug concentration remaining in the bead. As the drug concentration falls, so does the rate of diffusion through the membrane. The rate of release has been reported to be 1st order or declining exponentially with time. The diffusion of active ingredient through a membrane is described by the following equation: where:

$M_t/M_\infty$ = fraction dissolved at time $t$
k = rate constant
$M_t$ = mass of drug dissolved at time t
$M_\infty$ = mass of drug at time t=0

Dissolution profiles for film-coated beads show exponentially declining release rate profiles as stated by above equation.

The zero-order release kinetics is described by the following equation, which if satisfied would show that zero-order release has been obtained:

$$\frac{M_t}{M_\infty} = kt$$

This type of behavior has not been obtained with film-coated beads.

Attempts have been made to overcome this shortcoming of sustained-release drugs and yet very little success has been reported. A survey of patent literature suggests that attempts have been made to improve product release characteristics through use of a variety of polymers and polymer blends. These attempts have not succeeded in obtaining time-independent release rates, because the characteristic Fickian diffusion type of release has been found to predominate in spite of using a variety of polymers and blends.

Matrix Type of Delivery: The matrix type delivery devices consist primarily of an active agent finely dispersed in a monolithic matrix.

A flat slab of an eroding polymer containing a uniformly distributed drug has been reported to give zero-order release. The release kinetics, however, are reported to be dependent upon the system geometry. For sphperical matrices, this system does not give zero-order release.

In the case of a drug homogeneously dispersed in a noneroding matrix, the release rate has been found to be proportional to square root of time ($M=kt^{\frac{1}{2}}$, Higuchi Kinetics). More recently, research has focused on use of hydrogels in tablets. Zero-order release has reportedly been obtained through the use of concentration profiling of the drug inside the tablet matrix. (Professor Neil Graham and N. E. McNeill, University of Strathclyde, Glasgow, UK "Principles of the Design of Hydrogel-Containing Programmed Delivery Devices"—13th International Conference on Controlled Release of Bioactive Materials", Aug. 4, 1986, Norfolk, Va.).

Other approaches are also under study which focus on altering the structural characteristics in the hydrogels through cross linking, copolymerization, etc. (Roorda, W. E., et. al—"Zero-Order Release of Oxprenolol-HCl: A New Approach," Center for Bio-Pharmaceutical Sciences, Leyden University, Netherlands, presented at 13th International Conference on Controlled Release of Bioactive Materials, Aug. 4, 1986, Norfolk, Va.). The purpose of this research is to develop new polymers or modify existing ones such that a zero-order release can be obtained.

The present research approaches for matrix type systems appear to rely either on altering the structure of polymers or on the use of concentration profiling.

Reservoir Devices: In this approach, the active agent is uniformly dispersed in a suitable carrier and is encased in a membrane. As long as the active agent is in excess of the maximum solubility in the penetrant fluid, a constant thermodynamic activity is maintained across the outer membrane giving a zero-order release. As the active agent is depleted, the agent dissolves completely in the fluid, its activity falls off with time giving an exponential decline in release rate. (*Controlled Release Polymeric Formulations*, Paul, D. R. and Harris, F. W., ACS Symposium Series, ACS NY, Apr. 1976, Chapter 1).

Osmotic Devices: Alza company holds numerous patents for zero-order release of a drug via use of osmotic force. Water diffuses from the surrounding media to the tablet core and dissolves the drug. The drug solution does not diffuse out through the one-way membrane. Instead, like a pump, the solution oozes out from a single laser-drilled hole in the tablet under osmotic forces. The release rate is zero-order until 60–70% of the drug is released, followed by a declining rate of release. Alza's technology applies only to tablets and not to microencapsulated beads since it would be very expensive and technically difficult to drill precise holes in the microspheres.

Thus except for reservoir devices, zero-order release has reportedly not been achieved in case of microcapsules. Zero-order release with reservoir devices is obtained until no excess drug is left in contact with a saturated drug solution in the reservoir. A recent paper (M. Donbrow, School of Pharmacy, Jerusalem, Israel presented at the 13th International Symposium on Controlled-Release of Bioactive Materials, Aug. 3-6, 1986—Norfolk, Va.) states "Microcapsule release literature includes many unvalidated reports of exponential release, also some matrix release ($M=kt^{\frac{1}{2}}$ or Higuchi Kinetics), and dissolution rate-limiting release ($m^{\frac{1}{2}} \alpha\ t$), but very rarely zero-order release."

Pertinent examples of the above are disclosed in the following references:

U.S. Pat. No. 4,423,099 discloses non-uniform water-insoluble interpenetrating polymer blend compositions comprising a first permeable water swellable polymer substrate interpenetrated in a gradient substantially normal to the substrate surface by a second less permeable condensation polymer to form a diffusion rate controlling membrane therein. The resulting polymer blend is such that the concentration of the condensation polymer increases from 0% at the inner surface of the water swellable polymer to about 100% at the outer surface of the water swellable polymer. Such compositions are useful as polymers with reduced permeabilities for water and organic solvents and therefore for the controlled delivery of active ingredients such as fragrances and bio-affecting agents into air or aqueous environments, or in a membrane separation processes.

U.S. Pat. No. 4,177,056 discloses a controlled, sustained release composition comprising a pharmaceutically, insecticidally or herbicidally effective agent and a water-insoluble hydrophilic gel comprising: (A) about 30 to about 90% of a hydrophilic (a) polymer of identical or different water-soluble mono-olefinic monomers, or (b) copolymer of the water-soluble monomers with 1 to 70% of water-insoluble, identical or different mono-olefinic monomers, which polymer or copolymer is cross linked with (B) about 10 to about 70% of a terminal diolefinic hydrophobic macromer having a molecular weight from about 400 to about 8000.

U.S. Pat. No. 4,138,475 discloses a sustained release pharmaceutical composition consisting of a hard gelatine capsule containing film coated spheroids, the spheriods comprising propranolol or a pharmaceutically acceptable salt thereof, in admixture with a non-water swellable microcrystalline cellulose, with the spheroids having a film coat comprising ethylcellulose optionally together with hydroxypropyl methylcellulose and/or a plasticizer.

U.S. Pat. No. 3,845,770 issued to Theeuwes and Higuchi and well known to the prior art, describes an osmotic device for the zero-order release of an active agent. The osmotic device disclosed in this patent consists of an active agent enclosed in a semi-permeable wall. The semi-permeable wall is permeable to the passage of an external fluid but is substantially impermeable to the passage of the active agent in solution with the external fluid. An osmotic passageway is provided through the wall to deliver the solution of the active agent in the external fluid to the environment. The patent thus teaches the use of osmotic delivery of the active agent solution through a specially constructed passageway instead of delivery via diffusion through a membrane.

U.S. Pat. No. 4,327,725 describes a useful variation of the basic osmotic device. Patentees teach how to enhance the delivery kinetics of the basic osmotic pump via use of a hydrogel layer inside the semi-permeable membrane. The structure of the device consists of an active agent enclosed in a hydrogel layer which is enclosed by a semi-permeable membrane. The semi-permeable membrane allows diffusion of external fluid to inside but does not allow the diffusion of the solution of active agent in the external fluid to the surrounding environment. The hydrogel swells with absorption of external fluid and exerts pressure on the solution of active agent in the external fluid. The solution of the active agent in the external fluid is then delivered to the surrounding media through a single specially constructed passageway through the hydrogel layer and the membrane.

It is claimed that the variation described in U.S. Pat. No. 4,327,725 is particularly useful in case of drugs which are insoluble in the external fluid. The osmotic passageway in the device described in this patent is created by drilling a hole through the semi-permeable wall to connect the active agent compartment with the exterior of the device. A laser-machine is utilized to drill precise holes. This procedure is cumbersome and requires a considerable development effort to tailor the delivery system to each individual drug or active agent.

In case of all osmotic devices, whether a swellable polymer is utilized or not, the delivery mode is the release of the active agent through a specially constructed passageway/hole instead of diffusion through a membrane.

SUMMARY OF THE INVENTION

The present invention relates to a bioactive composition having a controlled, sustained release delivery pattern when contacted with a suitable surrounding media. The composition comprises a pharmaceutically, insecticidally, herbicidally or fertilizing bioactive material core, soluble in a given surrounding media, the core present in an amount at least sufficient for a total dosage during a treatment period; a first coating enveloping the bioactive material core comprising a polymer or a blend of polymers, said polymer or blend of polymers being swellable upon penetration by the surrounding media; and a second coating enveloping the first coating enveloped bioactive material core comprising a polymer or a blend of polymers; said polymer or blend of polymers being water-insoluble and forming a semi-permeable barrier permitting diffusion of the surrounding media into the first coating enveloped bioactive material core and also permitting the diffusion of the surrounding media dissolved bioactive material into the surrounding media. The first coating can further comprise a plasticizing agent. Examples of suitable first coating polymers are hydroxypropyl cellulose, hydroxypropyl methyl cellulose, polyvinyl alcohol or mixtures thereof. Examples of suitable second coating polymers are ethyl cellulose alone or in combination with hydroxypropyl cellulose or methyl cellulose.

The controlled, sustained release delivery pattern can be a zero-order or a bi-phasic pattern, these patterns are accomplished by modifying the thicknesses of the first and second coatings and the composition of the second coating. To achieve a zero-order pattern the first coating must be present in an effective thickness and the second coating must be present in an effective thickness and have a permeability so together they cooperate to cause the diffusion of penetrants through the first coating to be rate controlling. In addition, the second coating must have the requisite stretchability to prevent rupture of the second coating due to the swelling of the first coating. To achieve a bi-phasic pattern the first coating must be present in an effective thickness and the second coating must be present in an effective thickness and have a permeability so together they cooperate to cause the diffusion of penetrants through the first coating to be the rate controlling step. The second coating must have the requisite stretchability to prevent rupture of second coating due to the swelling of the first coating until a specific time in the release pattern. Other release patterns are available by modification of the coatings thicknesses and the amount of insolubles in the second coatings.

BRIEF DESCRIPTION OF THE DRAWING

FIG. 10 is a plot of dissolution release profiles for controlled release phenylpropanolamine hydrochlorides as observed in Run 5 of Example 5.

FIG. 11 is a plot of dissolution release profiles for controlled release phenylpropanolamine hydrochlorides as observed in Run 6 of Example 5.

DETAILED DISCUSSION OF THE INVENTION

The present invention is a coating formulation for the encapsulation of any bioactive material such as a pharmaceutical, pesticide, fertilizer, etc., which can be applied using the conventional film-coating technology. The coating formulation can be tailored to give first-order, fractional-order, zero-order, or biphasic release kinetics of the active ingredient when the encapsulated product is brought in contact with a liquid medium.

The coating formulation consists of two distinct films or layers or coatings, in which the inner-coat (also referred to as Coat I or the first coat) consists predominantly of a water-swellable and water-soluble polymer or polymer blends. The outer-coat (also referred to as Coat II or the second coat) consists of any suitable polymer, polymer blends, resins, plasticizers, etc., which can form a semi-permeable membrane completely surrounding Coat I while permitting diffusion of penetrant fluid and the solution of bioactive material in the penetrant fluid across the membrane. Both the coats are distinct, do not intermix and have a very distinct interface between them as opposed to the interpenetrating polymer network (IPN) films.

The dual-coat concept described above is capable of modifying the release kinetics of the active core ingredients irrespective of the method used for film-coating. According to the present invention, conventional pan coating, fluid-bed coating or centrifugal fluid-bed coating technology can be utilized to apply the coatings on the core of bioactive material.

The core to be encapsulated could be 100% active substance or could be in admixture with an inert binder or substrate. The core could be any size or shape provided the surface morphology permits application of even thickness of each coat all around the core. The preferred shape and size of the core is a spheroid having a 125-10,000 micron diameter.

Film coated delivery systems apply to those bioactive materials which are soluble to some extent in the surrouding media. Bioactive substances which are 100% insoluble in the surrounding media can not be made to give a controlled-release in conjunction with such devices. Sparingly soluble pharmaceuticals such as theophylline have been found to be completely acceptable as subject candidates with respect to our invention. Therefore, it appears that the lower limit of solubility for the candidate core substances is very low.

Figure 1:
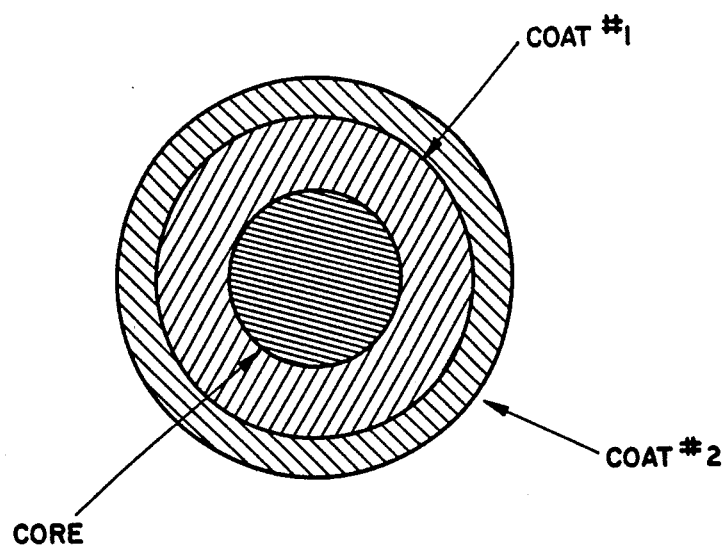
FIG. 1 is a diagram of dual-coating controlled, sustained release bioactive material composition.

The dual coat concept in which the inner layer is that of a water soluble, swellable polymer, and the outer layer is a water insoluble, semi-permeable membrane is illustrated in FIG. 1. The following examples are offered to demonstrate the efficacy of the present invention.

EXAMPLE 1

Increasing Thickness of Coat II

Spherical beads of Theophylline (active substance) were prepared in a CF granulator using standard techniques. These beads contained 33% Theophylline and 67% inert material, and were screened to collect beads of uniform size. 250 grams of beads passing through US mesh 30, but retained on US mesh 40 screen, were fluidized in a fluid-bed coater. This fluid bed coater operates at a slightly positive pressure. Heated $N_2$ gas was used to fluidize these beads. When the beads were heated to desirable process temperature (~145° F.), they were coated with a composition having the following formulation:

8.5 grams—Hydroxy Propyl Cellulose (HPC)
10.3 grams—Opadry® Film Coating Material (Grade YS-1-7006)*

*Opadry is a trademark of Colorcon 1.72 grams—Shellac
1.0 liters—200 proof Alcohol (ethyl alcohol)

The polymer spray was continued until the thickness of the coat was approximately 30% by weight of the starting material (spherical beads). The process conditions were as follows:

Temperature of Fluid Bed Solids=148° F.
Spray Rate=100 grams/hour

After the desired thickness was obtained, the coated beads were coated with a second composition having the following formulation:

25.0 grams—Ethyl Cellulose (EC)
3.3 grams—Dibutyl Sebacate (Plasticizer for EC)
4.0 grams—Shellac
1.0 liter—200 proof alcohol (ethyl alcohol)

During this second coating step, samples were withdrawn during the coating process after 2 wt % [identified as product A (30-2)], and 4 wt % [product A (30-4)] coating thickness was applied. These samples were then analyzed in a USP-approved dissolution tester.

Figure 2:
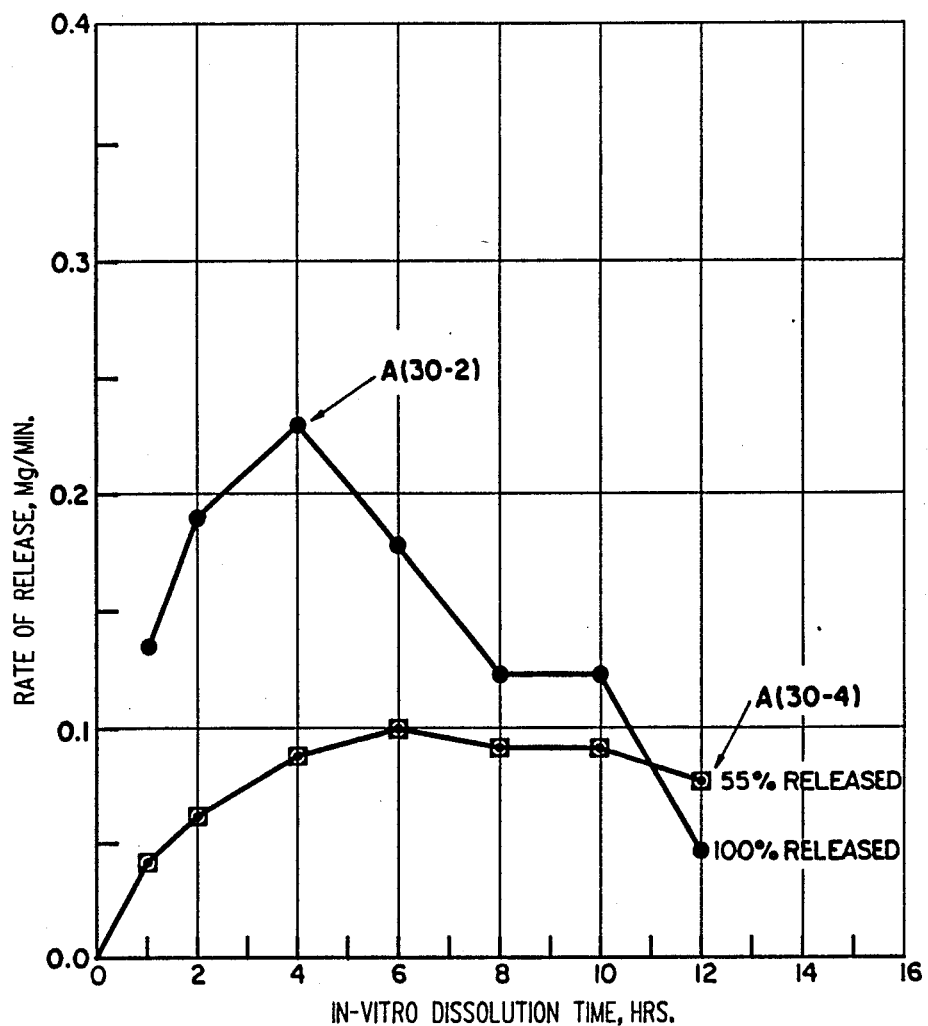
FIG. 2 is a plot of dissolution release profiles for controlled release theophylline produced in accord with the procedures set out in Example 1.

The test conditions in the USP dissolution tester (Van-Kel Dissolution apparatus and Beckman UV Spectrophotometer) were as follows:

Method=Paddle
RPM=100
Temperature=37° C.
Media=1.5 pH Water
Absorbances Measured at the wavelength of (λ)=270 nm The results of these dissolution tests are shown in FIG. 2. As seen in this figure, the 4 wt % coating thickness [product A(30-4)] gave a very close approach to a zero-order release over a twelve (12) hour period. The product with 30 wt % thickness of 1st coat-4 wt % thickness of second coat [product A(30-4)] is substantially superior to the product with 30 wt % thickness of first coat and 2 wt % thickness of second coat [product A(30-2)] in terms of approach to zero-order release.

EXAMPLE 2

Increasing Thickness of Coat I

The procedures of Example 1 were repeated in order to investigate the effect of differing the first coat thicknesses; the varied thicknesses are detailed in the following table. The second coat thickness was retained at 4 wt % as in Example 1.

| Product Identification | Thickness, % by Weight of Starting Material | |
| --- | --- | --- |
| | First Coat | Second Coat |
| A(16-4) | 16% | 4% |
| A(22-4) | 22% | 4% |

Figure 3:
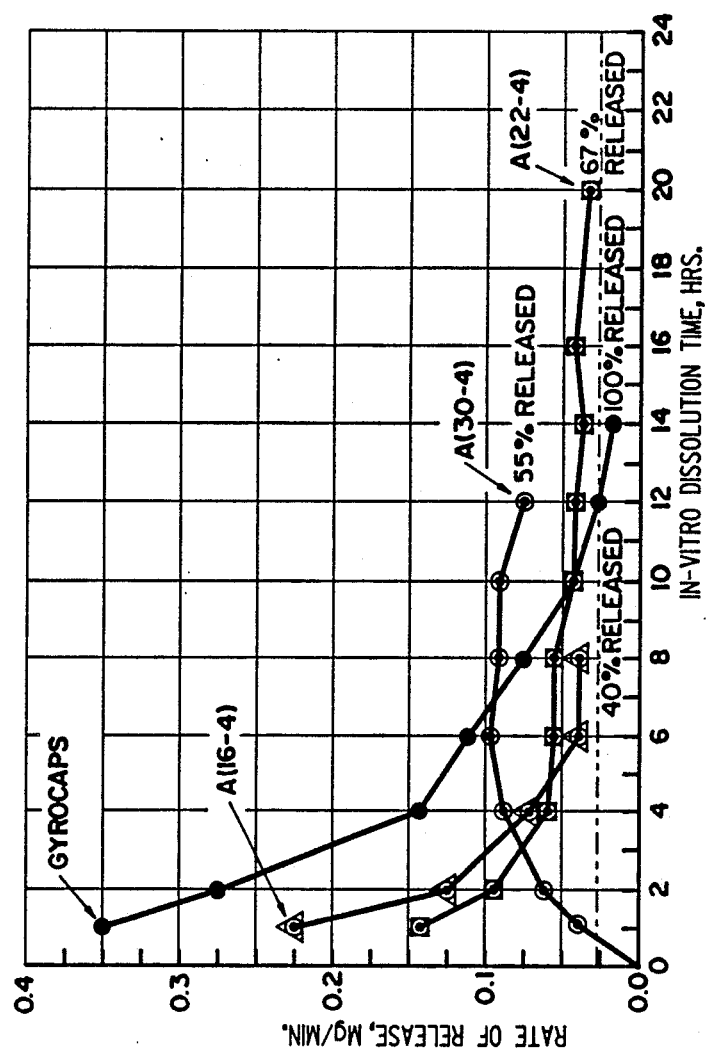
FIG. 3 is a plot of dissolution release profiles for controlled release theophylline produced in accord with the procedures set out in Example 2.

The resultant encapsulated beads were analyzed using the same dissolution test and procedure as before. The results obtained from this test are shown in FIG. 3. The release profile obtained with 30% first coat and 4% second coat [product (30-4)] is also shown in this figure.

For comparison, a leading time-release, GYROCAPS®-Slow Bid, 12 Hour, theophylline, available in the market was also tested in the same dissolution tester using the same conditions as above. The release profile obtained is also shown in the FIG. 3.

As seen in FIG. 3, all the three products made using the dual coat concept described above, provide a more nearly ideal zero order release pattern when compared to the GYROCAPS® theophylline. Products obtained with 22% thickness of first coat, 4% thickness of second coat [product A(22-4)], as well as 30% thickness of first coat, 4% thickness of second coat [product A(30-4)] are substantially superior to a typical sustained-release drug (e.g. GYROCAPS® theophylline) in the market.

EXAMPLE 3

Mixture of Batches

Figure 4:
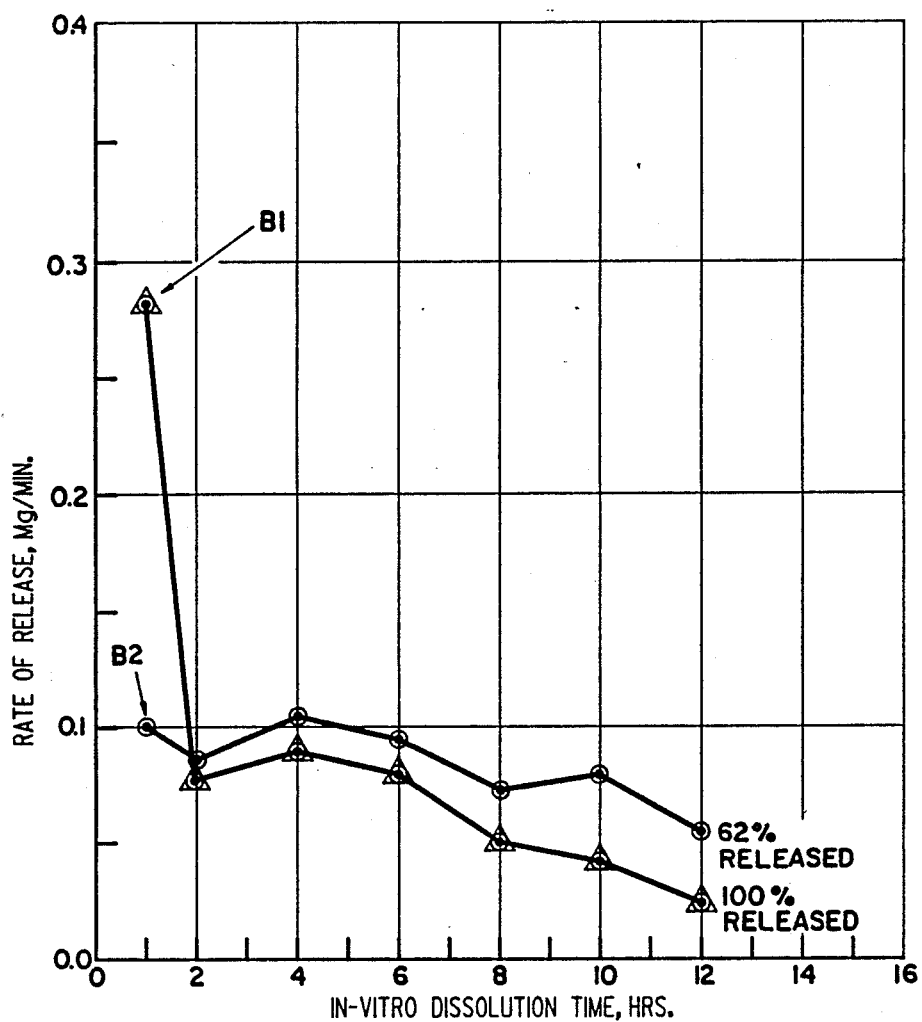
FIG. 4 is a plot of dissolution release profiles for controlled release theophylline produced in accord with the procedures set out in Example 3.

In order to determine the time-release profiles produceable by mixing beads with differing coating thicknesses together, the following example was prepared. In this example, two samples were prepared for dissolution testing using the following beads: 0 wt % Coat 1, 0 wt % Coat 2 [A(0-0)]; 30 wt % Coat 1, 0 wt % Coat 2 [A(30-0)]; 30 wt % Coat 1, 2 wt % Coat 2 [A(30-2)]; and 30 wt % Coat 1, 4 wt % Coat 2 [A(30-4)]. The first sample [B1] was a mixture of equal proportions of all four beads, while the second sample [B2] was mixed so as to produce a mixture having increasing proportions of the beads with the heavier outer coatings. The proportions of the mixtures of the two samples are listed in Table I below. FIG. 4 shows the release profiles obtained when products with different thicknesses of the second coat were mixed and tested in the dissolution tester.

TABLE I

| Product B1 Mix in Equal Proportions | | Product B2 Mix in Gradually Increasing Proportions | |
|---|---|---|---|
| Product | Wt % | Product | Wt % |
| A(0-0) | 25 | A(0-0) | 14 |
| A(30-0) | 25 | A(30-0) | 10 |
| A(30-2) | 25 | A(30-2) | 17 |
| A(30-4) | 25 | A(30-4) | 59 |
|  | 100 |  | 100 |

As can be seen, Product B2 closely approximates a zero-order release profile. Product B2 appears to be somewhat better than the product obtained with 30% first coat and 4% second coat [Product A(30-4) of Example 1 and FIG. 3] during the first 2-3 hours.

The purpose of displaying the curves B1 and B2 is to show that by mixing separate batches of the coated beads one can fine tune the release rate profile. Additionally, programmable release rates can be produced by adjusting the proportions of individual batches.

EXAMPLE 4

Effect of pH and RPM

In addition to providing a zero-order release profile, the delivery system for solid oral dosage forms should be capable of minimizing the effects of physiological variations that occur intra-subject as well as inter-subject. These variations are caused, for example, by the pH in the GI tract, metabolism rates, presence of food and enzymes, temperature, fluid-volume, etc. A drug delivery system that minimizes the effect of these variables on the release characteristics of active substances can provide better predictability and repeatability for a cross-section of subject population.

Example 4 is provided to demonstrate the effect of 'pH' of the media and paddle 'RPM' on the in-vitro dissolution profiles for theophylline beads encapsulated as described in Example 1.

Figure 5:
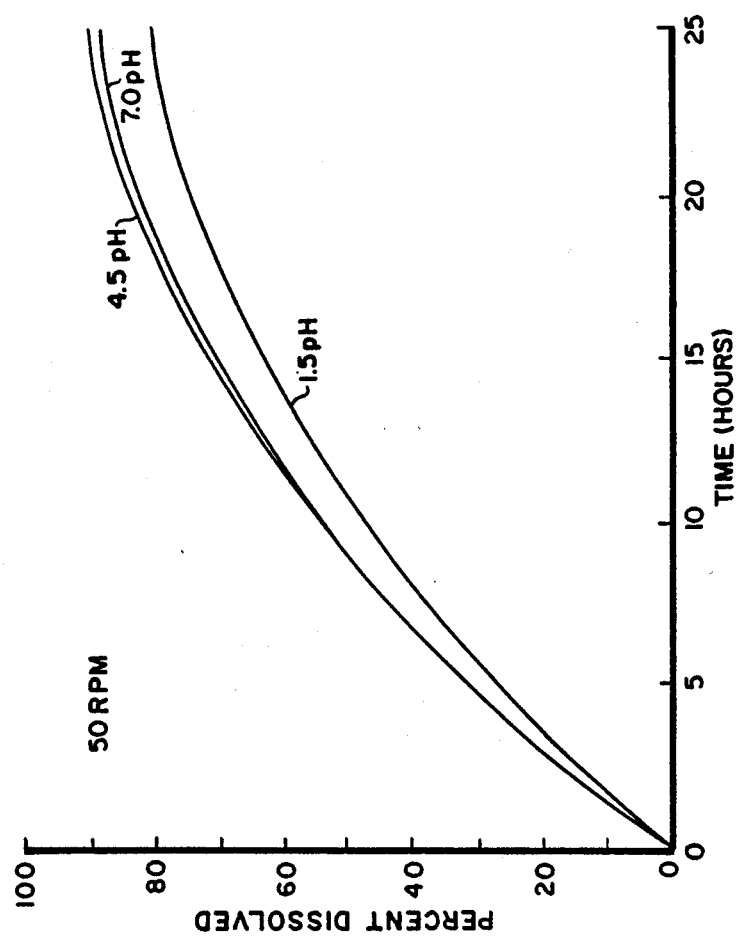
FIG. 5 is a plot of the effect of pH on the dissolution release profile of controlled release theophylline produced in accord with the procedures set out in Example 4.

To evaluate the effect of 'pH' on dissolution profiles, tests were carried out at different 'pH' of the media ranging from 1.5 to 7.0. FIG. 5 shows the variation in the dissolution profiles for pH's of 1.5, 4.5 and 7.0. The effect of 'pH' of the media on the in-vitro dissolution characteristics appears to be well within established acceptable limits.

To evaluate the effect of 'RPM' of the paddle on dissolution profiles, tests were carried out at 50 and 100 RPM. Table II shows the variation in % dissolved at 1.5 hrs. and 12 hrs. for 50 and 100 RPM. The variation in % dissolved with changes in RPM is significantly lower for the above product compared to that seen with the matrix-type sustained-release tablets.

TABLE II

| Effect of RPM on Dissolution | | |
|---|---|---|
| RPM | % Dissolved 1.5 Hours (1.5 pH) | % Dissolved 12 Hours (7.0 pH) |
| 50 | 5.9 | 48.5 |
| 100 | 6.6 | 59.0 |

Since the effect of RPM on dissolution characteristics appears to be minimal with the dual-coat approach, the resulting formulation is likely to be much more rugged and therefore more forgiving of manufacturing variations than that obtained with matrix type of delivery products.

In order to demonstrate the applicability of the present invention to a wide range of bead sizes and to a variety of active agents the following example was run.

EXAMPLE 5

Large Beads of Phenylpropanolamine

Examples 1-4 demonstrated the applicability of the dual-coat concept to theophylline, which is sparingly soluble in water and had an average bead size of 500 microns. To evaluate the dual coat concept over a wide range of drug solubilities, phenylpropanolamine hydrochloride (PPA), which is freely soluble in water, was selected as the active agent in Example 5.

Also, a much larger drug bead size—6,000 microns was selected. This would allow verification of the dual coat concept over a very wide range of bead sizes. Drug beads of such size could also be used in lieu of tablets, provided each bead contained the therapeutic dose level of the active agent.

Specification of Core Beads

The core bead of PPA used during the various pilot-plant runs reported in Example 5 was formulated according to the following specification:
Active Ingredient—Phenylpropanolamine Hydrochloride (PPA)
Core Bead Size—Spherical beads of 6,000 micron diameter
Core Bead Weight—Approximately 110 mg
Core Bead Composition—68.1 wt % PPA 6.4 wt % Methocel®*Hydroxypropyl Methyl Cellulose (HPMC) 25.5 wt % Starch/Sugar
*Methocel is a trademark of the Dow Chemical Company
Dosage Per Bead—Average 75 MG of PPA

Preparation of Core Beads

The core beads, whose specification is given above, were prepared in a granulator. Any other suitable method such as fluidized bed coating, pan coating could also be used to make the core beads. No further surface modifications are necessary when beads are properly made using these methods. The beads can be encapsulated using the dual-coat concept in any standard coating apparatuses including but not limited to a CF granulator, fluid-bed coater or pan coater.

Alternatively the core beads can be made by using an appropriately shaped die to minimize sharp edges on the surface of the core bead. In the event some sharp edges are left on the surface of core bead, a top coat of water soluble polymer may be applied on the core/tablet made from the die. The purpose of this water soluble coat would be to create a reasonably smooth surface morphology without interfering appreciably with the release characteristics of the active agent.

Method for Applying Film Coats

A fluid-bed coater was used to apply the film coats on the 6,000 micron PPA beads. Two coats were sequentially applied, however, the second coat was not applied until the first coat had been properly dried.

Description of the Coating Formulations

In accord with the present invention, the first coat is a predominantly water-soluble as well as a water-swellable polymer or a number of polymers. In addition, a water-soluble and swellable but alcohol insoluble polymer such as Hydroxypropyl Methyl Cellulose (HPMC) was added to the solution. The addition of an insoluble polymer to a polymeric solution helps to control the agglomeration of beads during the fluidized-bed coating process.

The second-coat is a mixture of water-soluble and water-insoluble polymers tailored to such proportions as to give the desired permeability to the outer coat. Appropriate plasticizers are added in each coat formulation to enhance the film qualities such as adhesion, spreading, uniformity, gloss, etc.

Although the mechanism that governs the rate and kinetics of release is not clear, it has been found through empirical experimentation that for a given choice of polymers, the following parameters are critical.

Thickness of 1st Coat
Thickness of 2nd Coat
% Soluble Polymer in 2nd Coat Table III shows the values of these critical variables which were tested in Example 3 in order to approach a zero-order release of PPA during in-vitro testing.

TABLE III

Values of Critical Formulation Parameters in Different Runs Cited in Example 5

| RUN | 1ST COAT (% BY WEIGHT OF BEAD TO BE COATED) | 2ND COAT | % SOLUBLE POLYMER IN THE 2ND COAT |
|---|---|---|---|
| 1 | 7 | 1–6% | 32.32 |
| 2 | 7 | 1–3 | 24.71 |
| 3 | 3.5 | 1–5 | 24.71 |
| 4 | 3.5 | 1–3 | 14.22 |
| 5 | 1.75 | 1–5 | 14.22 |
| 6 | 1.75 | 1–4 | 14.22 |

The composition of the first coat was identical from run to run and is given in Table IV.

TABLE IV

Coat 1 Formulation Composition

| | |
|---|---|
| Hydroxypropyl Cellulose (HPC) | 1.00 wt % |
| Opadry ® Film Coating Material (YS-1-7006) | 4.70 wt % |
| Rosin | 0.21 wt % |
| Ethyl Alcohol | 94.09 wt % |
| Ratio of Alcohol Solubles/Insolubles | 0.26 |
| % Swellable Polymer | >95% |

Thus as described before, the above formulation gave a workable mixture of water-soluble and swellable polymers which could be film-coated in a fluidized bed without process interruptions. Addition of a small quantity (e.g. <0.25 wt %) of Rosin appeared to improve the gloss and integrity of 1st coat.

The process conditions used for applying Coat I are summarized in Table V given below:

Table V

Weight of Batch=200 grams
Temperature of Solids in Fluidized Bed=135° F.
Spray rate=4.6 grams/minute
Drying Time After Completion of Film Coat=30 minutes The Coat II formulations was varied between the pilot plant runs as is reflected in the % solubles reported in Table III. The Coat II formulation utilized Ethyl Cellulose as the water-insoluble polymer. Dibutyl Sebacate was used as a plasticizer for Ethyl Cellulose. The soluble polymers in Coat II formulation consisted of Opadry ® brand of a film coating material consisting predominantly of Hydroxyl Propyl Methyl Cellulose (HPCM) and Rosin for Pilot Plant Runs 1 through 5. For Run 6, Hydroxy Propyl Cellulose and Methyl Cellulose were used as soluble polymers in the Coat II formulation.

Thus whereas the water-insoluble polymer in the Coat II was the same for all the PPA runs, the water-soluble polymers were changed after Run No. 5 for the purpose of evaluating their effects on dissolution characteristics.

The detailed compositions of Coat II formulation are provided in Table VI.

TABLE VI

Coat II Formulation Composition

| Run | Wt % | | | | | |
|---|---|---|---|---|---|---|
| | 1 | 2 | 3 | 4 | 5 | 6 |
| Ethyl Cellulose | 1.59 | 1.52 | 1.52 | 1.53 | 1.53 | 1.53 |
| Dibutyl Sebacate | 0.42 | 0.40 | 0.40 | 0.40 | 0.40 | 0.40 |
| Opadry ® (YS-1-7006) | 0.27 | 0.24 | 0.23 | 0.12 | 0.12 | 0 |
| Rosin | 0.69 | 0.39 | 0.39 | 0.20 | 0.20 | 0 |
| HPC | 0 | 0 | 0 | 0 | 0 | 0.20 |
| Methyl Cellulose | 0 | 0 | 0 | 0 | 0 | 0.12 |
| Ethyl Alcohol | 97.03 | 97.45 | 97.46 | 97.75 | 97.75 | 97.75 |
| Total | 100.00 | 100.00 | 100.00 | 100.00 | 100.00 | 100.00 |
| Dry Film Proportions | | | | | | |
| % Insoluble | 67.68 | 75.29 | 75.29 | 85.78 | 85.78 | 85.78 |
| % Soluble | 32.32 | 24.71 | 24.71 | 14.22 | 14.22 | 14.22 |
| Total | 100.00 | 100.00 | 100.00 | 100.00 | 100.00 | 100.00 |

The process conditions for applying the Coat II formulations are summarized below:

Weight of Batch=100 grams
Temperature of Solids in Fluidized Bed=135° F.
Spray Rate=3.7 grams/minute In-vitro Dissolution Profiles Six samples were withdrawn during the application of Coat II in each run after predetermined amounts of solution were sprayed on to the beads. These samples have been tagged as No. 1, 2, 3, 4, 5, 6 in each run with incremental thickness of Coat II.

Each of the above samples with varying thicknesses of Coat II was tested in a Van-Kel dissolution tester with Beckman UV spectrophotometer using the USP Paddle method. The test conditions were as follows:

RPM=100
Wavelength=215 nm
Temperature=37° C.
Media pH=7.0 pH

The dissolution profiles obtained for various pilot plant runs are presented below.

It is apparent from the dissolution profiles presented in the following section, that the kinetics of release (e.g. 1st order, zero-order, etc.) and the rate of release (gms/minute) are predominantly dependent upon an interplay of the following three variables for a given choice of polymers.

- Thickness of Coat I
- Thickness of Coat II
- Permeability of Coat II (or % Solubles in Coat II)

Run 1

Figure 6:
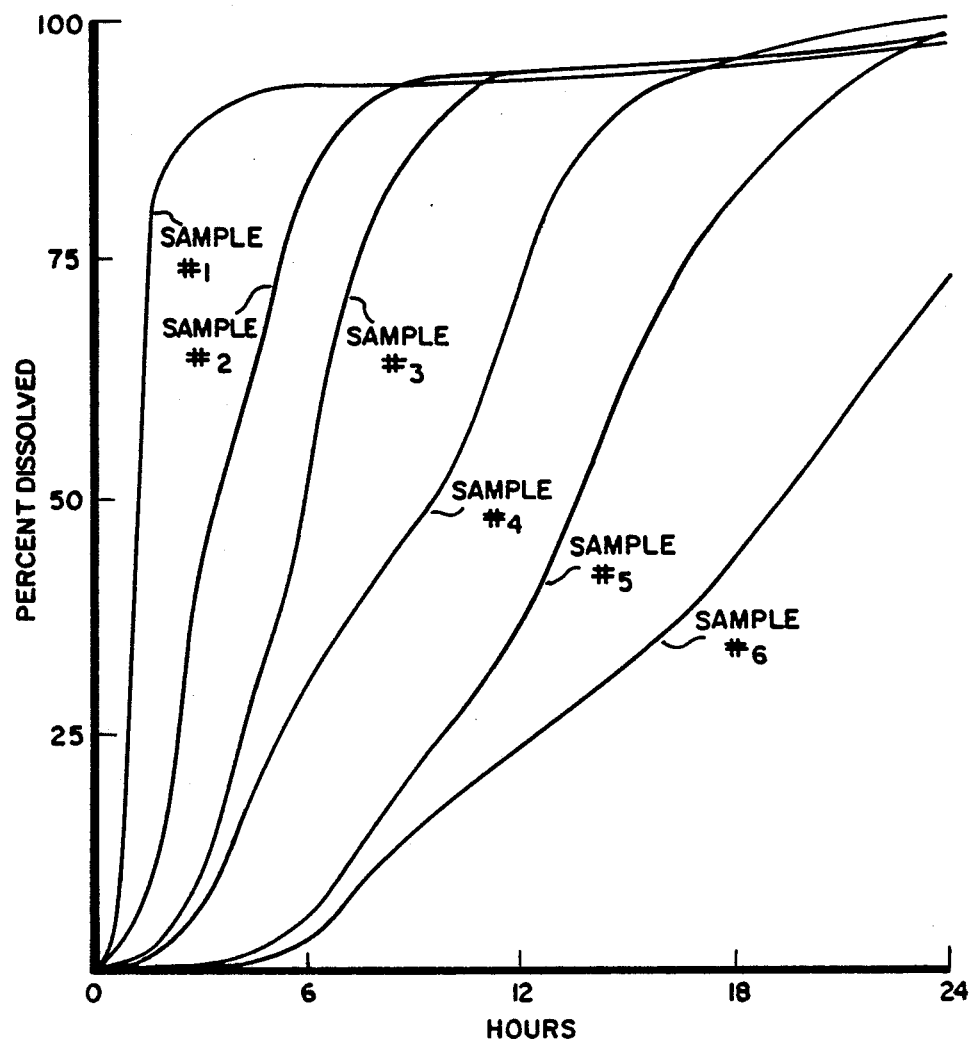
FIG. 6 is a plot of dissolution release profiles for controlled release phenylpropanolamine hydrochlorides as observed in Run 1 of Example 5.

Dissolution profiles for the following samples are shown in FIG. 6.

| Sample | Nominal Thickness 1st Coat (% by wt) | Nominal Thickness 2nd Coat (% by wt) | % Solubles in 2nd Coat (% by wt) |
|---|---|---|---|
| 1 | 7 | 1 | 32.32 |
| 2 | 7 | 2 | 32.32 |
| 3 | 7 | 3 | 32.32 |
| 4 | 7 | 4 | 32.32 |
| 5 | 7 | 5 | 32.32 |
| 6 | 7 | 6 | 32.32 |

Certain type of anomalous change in the shape of curve is seen in the middle of each dissolution profile. It is believed that this type of change in shape may have been caused by the relatively poor structure of the second coat. It is believed that with the 32.32% solubles in the second coat, the permeability may have been nonuniform leading to structural nonintegrity during the dissolution process.

Run 2

Figure 7:
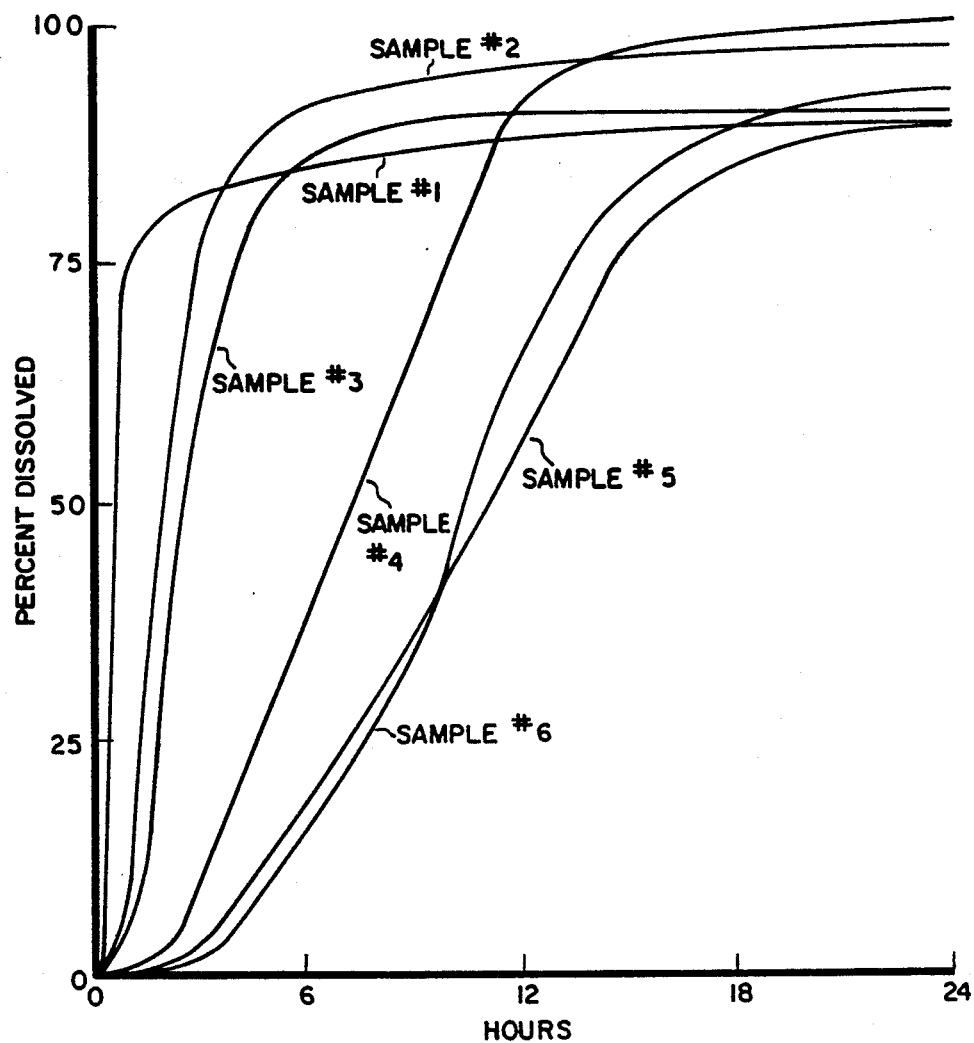
FIG. 7 is a plot of dissolution release profiles for controlled release phenylpropanolamine hydrochlorides as observed in Run 2 of Example 5.

This is a repeat of Run 1 except that the % soluble in second coat has been reduced from 32.32% to 24.71% as shown in Table VI. FIG. 7 shows the dissolution profiles for the following samples:

| Sample | Nominal Thickness 1st Coat (% by wt) | Nominal Thickness 2nd Coat (% by wt) | % Solubles (% by wt) |
|---|---|---|---|
| 1 | 7 | 0.5 | 24.71 |
| 2 | 7 | 1.0 | 24.71 |
| 3 | 7 | 1.5 | 24.71 |
| 4 | 7 | 2.0 | 24.71 |
| 5 | 7 | 2.5 | 24.71 |
| 6 | 7 | 3.0 | 24.71 |

As seen in FIG. 7, each dissolution profile gave a better approach to zero-order release compared to that shown in FIG. 6. It appears that the reduction in % soluble in the outer coat from 32.24 to 24.71% helps maintain the structural uniformity of the outer coat throughout the dissolution run and minimizes the anomalous behavior in the dissolution curve that was seen in FIG. 6.

Run 3

Figure 8:
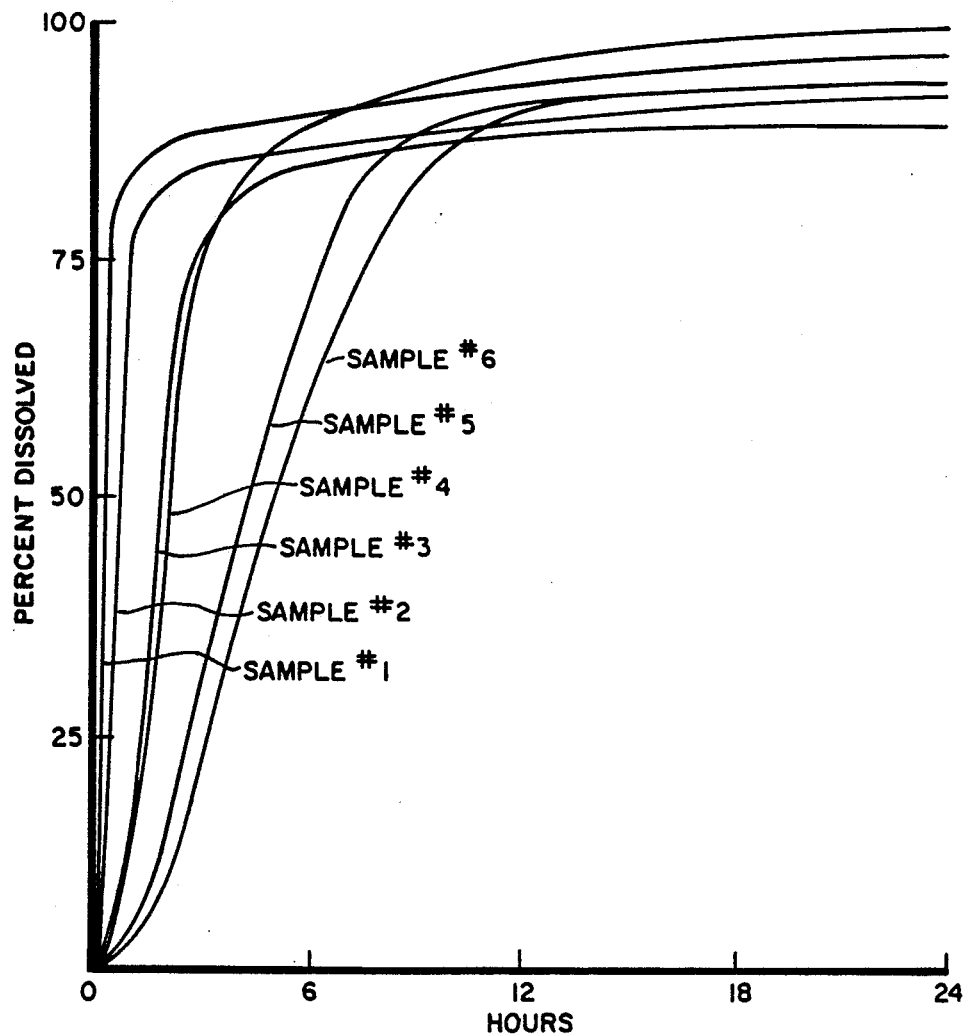
FIG. 8 is a plot of dissolution release profiles for controlled release phenylpropanolamine hydrochlorides as observed in Run 3 of Example 5.

This run shows the effect of reducing the thickness of first coat from 7% to 3.5% but keeping % solubles in second coat at the same level as Run 2 described above. FIG. 8 shows the dissolution profiles for the various samples stated below:

| Sample | Nominal Thickness 1st Coat (% by wt) | Nominal Thickness 2nd Coat (% by wt) | % Solubles in 2nd Coat (% by wt) |
|---|---|---|---|
| 1 | 3.5 | 1 | 24.76 |
| 2 | 3.5 | 2 | 24.76 |
| 3 | 3.5 | 3 | 24.76 |
| 4 | 3.5 | 3.5 | 24.76 |
| 5 | 3.5 | 4 | 24.76 |
| 6 | 3.5 | 5 | 24.76 |

Although the dissolution profiles with 3.5% thickness of 1st coat are similar to the ones seen in FIG. 7 with 7% of 1st coat, it is seen that the rate of dissolution is significantly faster for 3.5% thickness of 1st coat compared to 7% thickness of 1st coat. For example, the Sample 3 above (3.5 thickness of 1st coat, 3% thickness of 2nd coat) released most of its contents within 3 hours. Compared to this the sample with 7% thickness of 1st coat, 3% thickness of 2nd coat and similar % solubles in 2nd coat (Sample No. 6 in FIG. 7), released most of its contents in 16–17 hours.

This above comparison clearly shows the effect of thickness of 1st coat in controlling the rate of release of the active agent. It establishes that the first coat provides a rate limiting diffusion resistance in the overall delivery sequence. If the first coat were to merely squeeze the active agent out due to its expansion, as is the case of an osmotic pump, the rate of release would have been greater with greater thickness of first coat. As seen in the above example, the rate of release for 7% thickness of first coat is significantly less than the rate of release for 3.5% thickness of first coat.

Run 4

Figure 9:
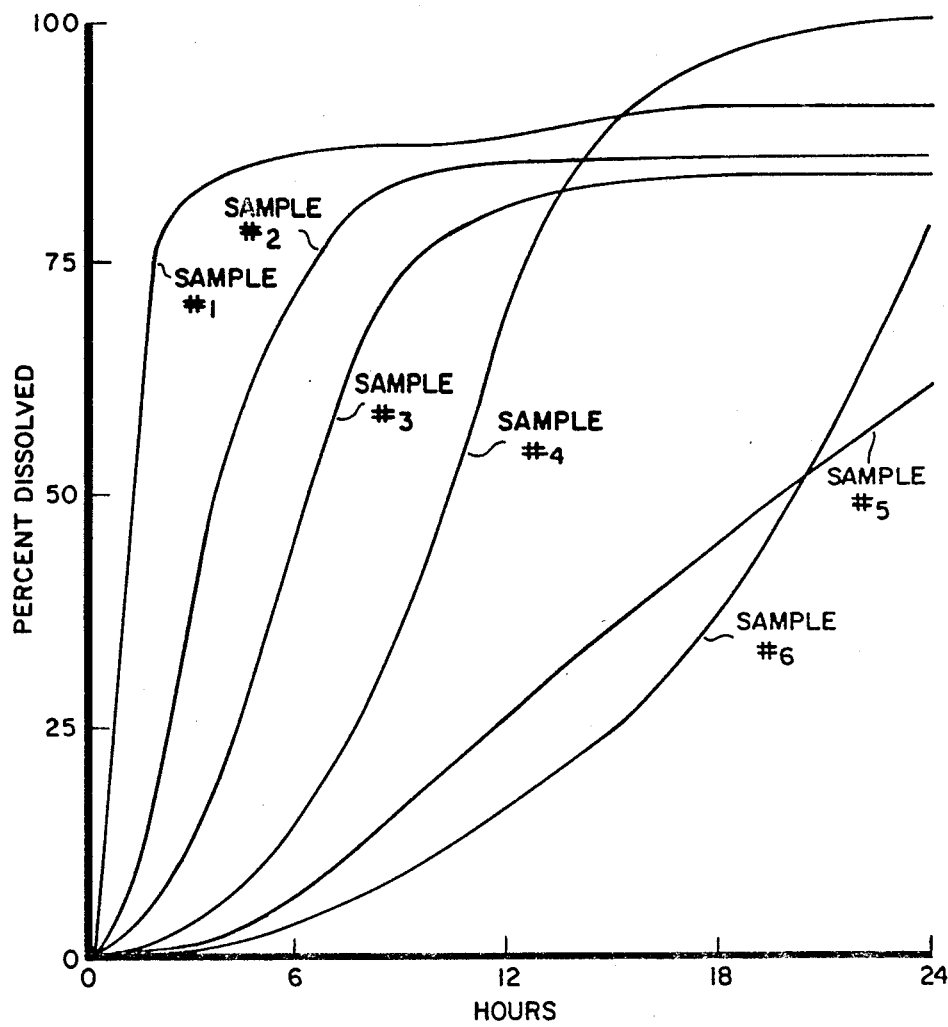
FIG. 9 is a plot of dissolution release profiles for controlled release phenylpropanolamine hydrochlorides as observed in Run 4 of Example 5.

This run shows the effect of reducing the % solubles in the Coat II from 24.76% (as in Run 3) to 14.13%. The dissolution profiles for the various samples collected during the Run 4 as shown in FIG. 9. The values of the critical parameters are given below.

| Sample | Nominal Thickness 1st Coat (% by wt) | Nominal Thickness 2nd Coat (% by wt) | % Solubles in 2nd Coat (% by wt) |
|---|---|---|---|
| 1 | 3.5 | 1.0 | 14.13 |
| 2 | 3.5 | 1.5 | 14.13 |
| 3 | 3.5 | 2.0 | 14.13 |
| 4 | 3.5 | 2.5 | 14.13 |
| 5 | 3.5 | 3.0 | 14.13 |
| 6 | 3.5 | 3.5 | 14.13 |

As seen in FIG. 9, the effect of reducing the % solubles from 24.76% to 14.13% is to cause the active ingredient to be released through a burst mechanism in a majority of samples tested above except Sample No. 5. Examination of Samples No. 4 and 6 after completion of the dissolution study clearly showed the rupture of outer shell into two halves. Sample No. 5 did not show any rupture. Thus, if the outer shell was strong enough to withstand internal pressures created by the swelling of Coat I, it would have given a close approach to zero order release of the active agent (PPA) in an aqueous medium.

Run 5

During this run, thickness of 1st coat was reduced further from 3.5% (as in Run 4) to 1.75%. As shown in Table VI, the % solubles in outer coat was maintained at 14.13% as in Run 4. FIG. 10 shows the dissolution profiles for the following samples generated during Run 5.

| Sample | Nominal Thickness 1st Coat (% by wt) | Nominal Thickness 2nd Coat (% by wt) | % Solubles in 2nd Coat (% by wt) |
|---|---|---|---|
| 1 | 1.75 | 1.0 | 14.13 |
| 2 | 1.75 | 2.0 | 14.13 |
| 3 | 1.75 | 3.0 | 14.13 |

-continued

| Sample | Nominal Thickness 1st Coat (% by wt) | Nominal Thickness 2nd Coat (% by wt) | % Solubles in 2nd Coat (% by wt) |
|---|---|---|---|
| 4 | 1.75 | 3.5 | 14.13 |
| 5 | 1.75 | 4.0 | 14.13 |
| 6 | 1.75 | 5.0 | 14.13 |

Comparison of FIG. 9 and 10 shows the effect of reducing the thickness of the first coating from 3.5 to 1.75%. None of the samples from Run 5, set out above, show any evidence that the outer shell had burst. It appears that keeping the same level of % solubles (14.13%) as in prior run (PP Run 4), and reducing the thickness of Coat I from 3.5% to 1.75% eliminated the burst effect and thereby gave close approach to a zero-order release.

For each sample, there is an initial delay after which the release of active agent starts. This initial delay could be very small as in the case of Sample 1 and 2 or could be large as in the case of Samples 5 and 6. The initial delay is dependent upon the thickness of both coats, the % soluble in outer coat and the type of soluble polymer used in outer coat for a given size core bead. The delay can be reduced if one were to switch to another soluble polymer in outer coat that dissolves faster than Rosin/HPMC combination that was used in runs mentioned above.

Run 6

This run shows the effect of using different soluble polymers in the outer coat in place of Rosin and Opadry ® brand of film coating material. The composition of the formulation for the outer coat in Run 6 is given in Table VI. FIG. 11 shows the dissolution profile for the following samples.

| Sample | Nominal Thickness 1st Coat (% by wt) | Nominal Thickness 2nd Coat (% by wt) | % Solubles in 2nd Coat (% by wt) |
|---|---|---|---|
| 1 | 1.75 | 1.0 | 14.13 |
| 2 | 1.75 | 2.0 | 14.13 |
| 3 | 1.75 | 3.0 | 14.13 |
| 4 | 1.75 | 3.5 | 14.13 |
| 5 | 1.75 | 4.0 | 14.13 |
| 6 | 1.75 | 5.0 | 14.13 |

Sample 2 in FIG. 11 shows that most of the drug is released within 14–15 hours when HPC/MC polymers are substituted for Rosin/HPMC polymers in the outer coat. In FIG. 10, Sample 2 shows that most of the drug is released within 9–10 hours. Also it is seen that with HPC/MC polymers the initial delays are considerably lower for various thicknesses of outer coat compared to that seen in case of Rosin/HPMC polymers in the outer coat.

The purpose of showing this comparison is to demonstrate that the release rates as well as initial delay times are also subject to the types of polymers used. However, the dual coating of the present invention broadly emcompasses using a variety of polymers which satisfy the polymer characteristics (solubility and swelling).

Important Observations based on Examples 1 through 5

For a given choice of active ingredient, the dosage strength, the dual-coating of the present invention can be used to obtain a radically different release rate characteristic than typically seen with the film coating approach.

In the limiting case, if the thickness of 1st coat is zero, the 1st order release kinetics of a simple monolayer are observed. As the thicknesses of the first and second coats are increased, the release order drops below 1. As the thicknesses of the first and second coats are further increased, the release order becomes zero and stays there as long as the structural integrity of the outer semi-permeable membrane is maintained. If however the outer coat were to gradually rupture, an increasing release rate is observed.

Zero-order release is but a special case of this physical phenomenon. The thicknesses of the first and second coats and the % solubles in the second coat which give zero-order release are dependent upon the selection of polymers and the size of the core-bead as shown in Table VII given below.

TABLE VII

| | Zero-Order Release Theophylline (Example 1 & 2) | Zero-Order Release Phenylpropanolamine HCl (PPA) (Example 5) 6,000 microns | | | |
|---|---|---|---|---|---|
| Bead Size: | 500 Microns | (I) | (II) | (III) | (IV) |
| Nominal Thicknesses (wt % of bead core) | | | | | |
| 1st Coat | 32 | 7 | 3.5 | 1.75 | 1.25 |
| 2nd Coat | 3 | 1–6 | 1–5 | 1–5 | 1–4 |
| Nominal % Solubles in 2nd Coat | 24 | 32 | 24 | 14 | 14 |

As seen in the above table for Example 5, there is more than one combination possible to obtain zero-order release kinetics for a given system. Each combination from I to IV gives a constant but a different rate of release.

Summary of Formulation Specifications

Physical and General Characteristics of the Core:

Any active substance, including but not limited to drugs, herbicides, pesticides, catalysts, fertilizers, which is at least very sparingly soluble in the surrounding media is applicable for use in the present invention.

Any size and shape of core bead provided surface morphology is smooth enough to permit deposition of an even coat all around the surface during the encapsulation process is applicable for use in the present invention.

Physical and General Characteristics of the Formulation:

Coat I Film: Predominantly consists of a polymer or blends which swells upon penetration by the surrounding media, e.g. Hydroxypropyl Cellulose (HPC), Hydroxypropyl Methyl Cellulose (HPMC), and Polyvinyl Alcohol (PVOH). These polymers can be in an admixture with plasticizers and/or other additives.

Coat II Film: A polymer or blend which forms a semi-permeable barrier to the diffusion of surrounding media into the core and which forms a diffusion barrier for the dissolved active substance, thus restricting its release into the surrounding media, e.g. Ethyl Cellulose (EC), Ethyl Cellulose+Hydroxy Propyl Cellulose, and Ethyl Cellulose+Methyl Cellulose.

Physical and General Characteristics of the Product:

In the case of pharmaceuticals, microencapsulated beads may be capsulated or tableted or encapsulated macrobeads may be used in lieu of tablets.

In case of fertilizers and pesticides, the product could be in powder form or in a macrosize tablet or any other suitable form consisting of encapsulated cores.

Preferred Range of Proportions of Ingredients:

The critical formulation specification is the formation of two distinct coats in which the inner coat is predominantly media soluble and swellable polymer and the outer coat is a semi-permeable polymer permitting diffusion of media as well as solution of active substance in the media in either direction.

For the given choice of active agent and polymers used in Coat I and Coat II, following variables are critical: size and composition of core bead, thickness of Coat I, thickness of Coat II, and permeability of Coat II (or % solubles in Coat II).

Depending upon the values of these critical parameters, one may encounter the following kinetic behavior:

First Order: Thickness of Coat I approaches zero

Zero-Order: Thickness of Coat I is high enough to cause the diffusion of penetrants through Coat I to be the rate controlling step. Coat II has sufficient thickness and stretchability to ensure that it does not rupture due to the swelling of Coat I. The thickness of coat II is sufficiently high and its permeability sufficiently low to ensure that the rate of diffusion of external fluid through the outer membrane (coat II) causes only a very gradual swelling of coat I that will last at least over the entire length of the dosage interval.

Fractional-Order: Thicknesses of Coat I and Coat II are intermediate between that for first-order and that for zero-order.

Bi-phasic: Thickness of Coat II is such that the buildup in hydrostatic forces due to the swelling of Coat I causes rupture in Coat II at a certain time in the dissolution curve leading to relatively rapid release thereafter.

The values of critical variables are dependent upon the system. There are several combinations which can give any of the above type of behavior. Since all these variables and their impact on release kinetics is interrelated, it is impossible to define the range of preferred proportions for the critical variables. Instead their range can be defined in terms of boundary conditions. For a zero-order release, these boundary conditions are stated below.

Zero-order release is obtained when the thickness of Coat I and coat II are high enough and the permeability of Coat II is low enough that:
- Swelling of Coat I is gradual which lasts at least until the majority of the drug is released.
- Coat II stretches but does not alter its structure physically or chemically.
- Coat II limits the rate of diffusion of external fluid to a point where the overall diffusion process is controlled by the rate of swelling of Coat I.

In this way, the critical formulation variables listed above are interdependent. This is amply illustrated by the various examples given above.

The mechanism by which the dual coat concept gives zero-order release is very complicated and not thoroughly understood. And although not wishing to be bound by any particular theory, the following explanation is offered.

Coat I, which is the inner coat, consists of a swellable polymer which swells upon the diffusion of penetrant fluid. Coat II, which is the outer semi-permeable membrane, acts not only as a containment device holding the inner swellable/soluble polymer in place, but also controls the rate of diffusion of penetrant to the Coat I.

When the dual-coated product is placed in a surrounding medium such as water, the water-penetrant diffuses through Coat II at a rate, which is controlled by Coat II's thickness and permeability, and Coat I starts to swell due to the penetrant's absorption, this absorption takes place at a controlled rate. Part of the penetrant diffuses through Coat I and hydrates (dissolves) the active material in the core producing a solution of active material dissolved in the penetrant. This solution diffuses through the Coat I, which is swelling and through the semi-permeable membrane (Coat II) to the surrounding media and is thus released.

As is evident, the dual coat system has several diffusion rate steps in series which determine the overall rate of release of the active ingredient. Depending upon the thicknesses of the coatings and the permeability of Coat II, any of these rates can be changed. Thus, for a given thickness of Coat I, the thickness of Coat II can be increased or permeability of Coat II can be reduced or both to make the diffusion of penetrant through the Coat I (which is controlled by the swelling of Coat I) rate-controlling. Conversely, for a given Coat II thickness and permeability, the thickness of Coat I can be increased to make the diffusion of penetrant through the Coat I (which is controlled in turn by the swellable rate of Coat I) rate-controlling. For reasons not fully understood, the combination of coatings leads to the zero-order release kinetics for the active ingredient, irrespective of the depleting concentrations of the active agent inside the microcapsule. As a result, zero-order release is seen over a much longer fractional span compared to that observed in case of some other zero-order release technologies.

If the thickness of Coat II is zero, the polymer in Coat I dissolves almost instantaneously and therefore the overall release is not much different from that seen with immediate release. Thus, a single monolayer of commonly available media soluble and swellable polymer by itself is not sufficient to give desirable sustained-release characteristics to a bead of active substance.

If thickness of Coat I is zero, the release rate is the typical first-order.

If the thicknesses of Coat I and Coat II are such that the rate of diffusion through Coat I is comparable to the rate of diffusion through Coat II, then fractional order (between 0 and 1) release is obtained. If the thicknesses of Coat I and Coat II are such that diffusion through Coat I is rate controlling, then zero-order release is obtained provided Coat II does not rupture under hydrostatic pressure exerted by the swelling of Coat I. Diffusion through Coat I becomes rate controlling when the rate of swelling of Coat I is low enough to dominate the overall release process.

In the event that Coat II ruptures at a certain point in the dissolution profile, sudden release of the remainder of the active agent is obtained. This type of biphasic delivery may have practical applications in programmable-release type products, e.g., latter-day delivery appetite supressants.

Coat II, the outer diffusion layer, also helps to minimize the effect of physiological variables in the body such as rate of shear/metabolism (simulated by RPM in the dissolution tests) by insulating the inner dissoluable and erodable layer of polymer from the turbulence and other fluid movements. The outer diffusion layer also provides the means to minimize the effect of other physiological variables in the GI tract such as pH, temperature, presence of enzymes, effect of food, GI fluid volume, etc.

In summary, following factors appear to contribute towards obtaining a zero-order release rate:

A. The thickness of Coat I should be sufficient enough that the rate of diffusion of the penetrant in Coat I dominates the overall rate of release.

B. The thickness and strength of Coat II should be selected to prevent any fracturing of Coat II by the swelling of Coat I. The thickness of Coat II should by high enough and permeability of Coat II should be low enough that at a given instant of time the inner swellable polymer of Coat I comes in contact with a limited amount of penetrant which gives rise to a swelling dominated release rate.

The above provides a list of most important control variables, which have an effect on the rate and kinetics of release of a bioactive material from a dual-coated bead. Compared to other conventional delivery systems, the dual coat formulation concept provides a greater number of control varaibles, which can be manipulated to specifically tailor a release profile.

The present invention has been described with reference to specific embodiments thereof. These embodiments are not meant to be a limitation of the scope of the present invention, such scope being determined from the following claims.

I claim:

1. A bioactive composition having a controlled, sustained release delivery pattern when contacted with a suitable surrounding media comprising:
    (a) a pharmaceutically, insecticidally, herbicidally or fertilizing bioactive material core, soluble in the surrounding media, the core present in an amount at least sufficient for a total dosage during a specified treatment period;
    (b) a first coating enveloping the bioactive material core comprising a polymer or a blend of polymers, said polymer or blend of polymers being water-soluble and swellable upon penetration by the surrounding media; and
    (c) a second coating enveloping the first coating, the second coating comprising a polymer or a blend of polymers; said polymer or blend of polymers being water-insoluble and forming a semi-permeable barrier permitting inward diffusion of the surrounding media and outward diffusion of the bioactive material dissolved in the surrouding media; whereby when the composition is exposed to the surrounding media, the exposure will result in the controlled release of the bioactive material.

2. The composition of claim 1 wherein the first coating further comprises a plasticizing agent.

3. The composition of claim 1 wherein the controlled, sustained release delivery pattern is a zero-order pattern and wherein the first coating is present in an effective thickness and wherein the second coating is present in an effective thickness and permeability so as to cause the diffusion of penetrants through the first coating to be the rate controlling step and wherein the second coating has the requisite stretchability to prevent rupture of the second coating due to the swelling of the first coating.

4. The composition of claim 1 wherein the controlled, sustained release delivery pattern is a bi-phasic pattern and wherein the first coating is present in an effective thickness and wherein the second coating is present in efffective thickness and permeability so as to cause the diffusion of penetrants through the first coating to be the rate controlling step and wherein the second coating has the requisite stretchability to prevent rupture of second coating due to the swelling of the first coating until a specific time in the release pattern.

5. The composition of claim 1 wherein the first coating polymer or blend of polymers, which are water-soluble and swellable, is selected from the group consisting of hydroxypropyl cellulose, hydroxypropyl methyl cellulose, polyvinyl alcohol, polyvinyl pyrrolidone and mixtures thereof.

6. The composition of claim 1 wherein the second coating polymer or blend of polymers is selected from the group consisting of ethyl cellulose, ethyl cellulose and hydroxypropyl cellulose, ethyl cellulose and methyl cellulose, and ethyl cellulose and hydroxypropyl cellulose hydroxypropyl methyl cellulose and rosin.

* * * * *